(12) United States Patent
Yap

(10) Patent No.: US 12,741,158 B1
(45) Date of Patent: Sep. 22, 2026

(54) MODULAR EXTRACORPOREAL LIGHT-BASED THERAPY SYSTEM FOR SEPSIS AND CARBON MONOXIDE POISONING

(71) Applicant: ZY Consulting LLC, Wilmington, DE (US)

(72) Inventor: Ernie Yap, Long Island City, NY (US)

(73) Assignee: ZY CONSULTING LLC, Wilmington, DE (US)

( * ) Notice: Subject to any disclaimer, the term of this patent is extended or adjusted under 35 U.S.C. 154(b) by 0 days.

(21) Appl. No.: 19/245,619

(22) Filed: Jun. 23, 2025

(51) Int. Cl.
*A61N 5/06* (2006.01)
*A61L 103/09* (2026.01)

(52) U.S. Cl.
CPC ........ *A61N 5/0624* (2013.01); *A61L 2103/09* (2026.01); *A61N 2005/0661* (2013.01); *A61N 2005/0663* (2013.01)

(58) Field of Classification Search
CPC ............. A61L 2103/05; A61L 2103/09; A61N 5/0624; A61N 2005/0661; A61N 2005/0663; A61M 1/302–303; A61M 1/3681–3686
See application file for complete search history.

(56) References Cited

U.S. PATENT DOCUMENTS 8,883,409 B1 * 11/2014 Ben-Hur ................ A61K 35/14 435/2
2004/0185426 A1 * 9/2004 Mallett ............... A61M 1/3472 604/20
2009/0149923 A1 * 6/2009 Herekar .................. A61F 9/008 607/88
2017/0100494 A1 * 4/2017 Dobrinsky ........... A23B 11/164
(Continued)

OTHER PUBLICATIONS

Kim et al., Light-based Methods for Whole Blood Bacterial Inactivation Enabled by a Recirculating Flow System, Photochem Photobiol. Mar. 31, 2018;94(4):744-751 (Year: 2018).*

*Primary Examiner* — Susan S Su
(74) *Attorney, Agent, or Firm* — HOLLAND & HART LLP

(57) ABSTRACT

A modular extracorporeal phototherapy system is disclosed for the treatment of both sepsis and carbon monoxide (CO) poisoning in critical care settings. The invention integrates ultraviolet C (UV-C) irradiation (250-270 nm) for pathogen inactivation and immune modulation, with visible light exposure (420-450 nm and 540-580 nm) to facilitate photodissociation of CO from hemoglobin and cytochrome oxidase. The device comprises a treatment chamber incorporated into a extracorporeal blood circuit, equipped with tunable or dual-mode light emitters and feedback-controlled dosing. The system features integrated real-time biomarker monitoring of reactive oxygen species (ROS), cytokines, and carboxyhemoglobin (CO-Hb) levels to optimize light dosage and treatment timing. Through shared hardware and software infrastructure, this system allows condition-specific treatment protocols using wavelength-targeted light therapy, enhancing clinical versatility and patient outcomes. Through shared hardware and software infrastructure, this system allows condition-specific treatment protocols using wavelength-targeted light therapy, enhancing clinical versatility and patient outcome.

8 Claims, 3 Drawing Sheets

(56) References Cited

U.S. PATENT DOCUMENTS

| | | | | |
|---|---|---|---|---|
| 2022/0016439 | A1* | 1/2022 | Shah | A61N 5/0624 |
| 2023/0380034 | A1* | 11/2023 | Allen, Jr. | H05B 45/325 |
| 2024/0024556 | A1* | 1/2024 | Gosney | A61L 2/10 |
| 2025/0319323 | A1* | 10/2025 | Richelieu | G02B 23/2469 |

* cited by examiner

MODULAR EXTRACORPOREAL LIGHT-BASED THERAPY SYSTEM FOR SEPSIS AND CARBON MONOXIDE POISONING

TECHNICAL FIELD

The embodiments generally relate to medical devices and therapeutic methods, and more particularly to a modular system using ultraviolet and visible light wavelengths for the treatment of sepsis and carbon monoxide poisoning through targeted extracorporeal blood irradiation.

BACKGROUND

Sepsis remains a leading cause of mortality worldwide, frequently progressing to multi-organ failure despite aggressive antimicrobial therapy and supportive care. Traditional extracorporeal blood treatment systems such as hemodialysis, hemofiltration, and plasmapheresis offer toxin and fluid removal but do not address circulating pathogens or immune dysfunction directly.

Separately, carbon monoxide (CO) poisoning, caused by CO binding to hemoglobin and mitochondrial enzymes, leads to hypoxia and impaired cellular respiration. Current treatments are supportive in nature, including normobaric and hyperbaric oxygen, but remain limited by relatively slow CO elimination.

Conventional extracorporeal blood treatment systems are widely used in clinical settings to support patients with impaired renal function, manage blood-borne conditions, or perform therapeutic plasma exchange. These systems operate by diverting blood outside of the body through a circuit that typically includes a dialysis filter or similar device to remove waste, toxins, or plasma components before returning the treated blood to the patient. Technologies such as hemodialysis, hemofiltration, hemodiafiltration, and plasmapheresis represent standard methods of extracorporeal therapy, each with specialized equipment designed to maintain appropriate flow rates, preserve blood cell integrity, and support continuous circulation throughout treatment durations.

In clinical and laboratory environments, ultraviolet-C (UV-C) has been used to disinfect equipment, surfaces, and fluids. Some historical approaches have involved extracorporeal exposure of blood to UV radiation, but implementation in modern clinical workflows has been limited due to concerns over cell viability, dosage control, and safe integration with existing treatment systems. Conventional technologies typically do not apply UV-C irradiation directly to blood during ongoing renal replacement therapy, and existing systems often lack real-time control over exposure parameters in dynamic blood flow environments. While UV-C irradiation has a longstanding history in pathogen inactivation, its use in whole-blood applications has been constrained by potential cytotoxicity and the absence of fine exposure control. Similarly, visible-light-driven photodissociation of CO from hemoglobin has been demonstrated in experimental settings but lacks integration into clinical extracorporeal devices. This invention addresses both challenges by leveraging real-time biomarker feedback and wavelength-specific emitters within a shared extracorporeal platform.

SUMMARY

This summary is provided to introduce a variety of concepts in a simplified form that is further disclosed in the detailed description of the embodiments. This summary is not intended to identify key or essential inventive concepts of the claimed subject matter, nor is it intended to determine the scope of the claimed subject matter. The disclosed invention comprises a unified system capable of delivering phototherapy to blood outside the body, tailored for sepsis or CO poisoning through wavelength-specific emitters. A treatment chamber positioned within a standard extracorporeal blood circuit—used in dialysis, hemofiltration, or plasmapheresis—provides controlled exposure to:

- UV-C light (250-270 nm) for sepsis, targeting pathogens and modulating immune cells (e.g., neutrophils) through sub-apoptotic doses.
- Visible light (420-450 nm and 540-580 nm) for CO poisoning, dissociating CO from cytochrome oxidase and hemoglobin, respectively.

A microprocessor-based controller regulates irradiance, exposure duration, and treatment modes based on real-time feedback from sensors monitoring immune markers (e.g., ROS) or CO-Hb levels. Closed-loop algorithms adjust light intensity, exposure duration, and emitter mode selection based on patient-specific feedback. The chamber supports both dialysis/hemofiltration and ECMO integration, making the platform adaptable to varied critical care workflows. Dual-wavelength emitters are modular and may be swapped depending on the targeted pathology.

This integration of feedback-controlled phototherapy enables dynamic response to patient biomarkers, mitigates overtreatment risks, and provides enhanced clearance of infection and toxic gases from the bloodstream.

A system and method for UV-C and visible light irradiation of extracorporeal blood enables targeted pathogen inactivation, immune modulation to treat sepsis and therapeutic dissociation of CO from hemoproteins for CO poisoning cases, respectively. The system includes a treatment chamber integrated within a conventional extracorporeal circuit and exposes blood to electromagnetic radiation of selected wavelengths. UV-C radiation is applied within the 250 to 270 nanometer range for pathogen inactivation and immune signaling, while visible light in the 420-450 nm and 540-580 nm ranges is used to disrupt CO binding to cytochrome oxidase and hemoglobin, respectively.

The system includes a light emitter array and chamber designed to accommodate blood flow at clinical rates, and deliver wavelengths tailored to therapeutic targets. For CO poisoning, the system uses dual-wavelength emitters in the blue (420-450 nm) and green-yellow (540-580 nm) spectra to break the CO-heme bond in cytochrome oxidase and carboxyhemoglobin. Exposure is calibrated to deliver between 5-15 J/cm$^2$ per pass, with irradiance levels of 100-250 mW/cm$^2$ over small-diameter, transparent tubing to optimize penetration and dissociation efficiency.

In sepsis applications, the same extracorporeal circuit allows for real-time immune modulation using UV-C irradiation. Blood is treated in an enclosed chamber using UV-transparent materials, such as quartz or fluoropolymers, and irradiated with 5-10 mJ/cm$^2$ to stimulate neutrophil ROS generation and immune function. A controller adjusts exposure time using feedback from biosensors and patient-specific parameters such as flow rate, hematocrit, and sepsis biomarkers.

The system may operate in pulse or continuous mode and can incorporate cooling and reflective shielding to prevent heating or environmental exposure. The chamber geometry and emitter configuration may include a cylindrical light bath or a coiled tubing design. Multiple passes or recirculation may be employed, particularly for CO clearance, with integrated co-oximetry used to monitor CO-Hb dissociation in real-time.

By extending the functionality of extracorporeal light exposure beyond microbial control to include gas-to-heme dissociation, the disclosed system enables rapid intervention in carbon monoxide poisoning cases. This dual-use capability broadens the clinical utility of the platform and allows for precision modulation of immune function and oxygen-carrying capacity in critical care settings.

Other illustrative variations within the scope of the invention will become apparent from the detailed description provided hereinafter. The detailed description and enumerated variations, while disclosing optional variations, are intended for purposes of illustration only and are not intended to limit the scope of the invention.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein.

DETAILED DESCRIPTION

Figure 1:
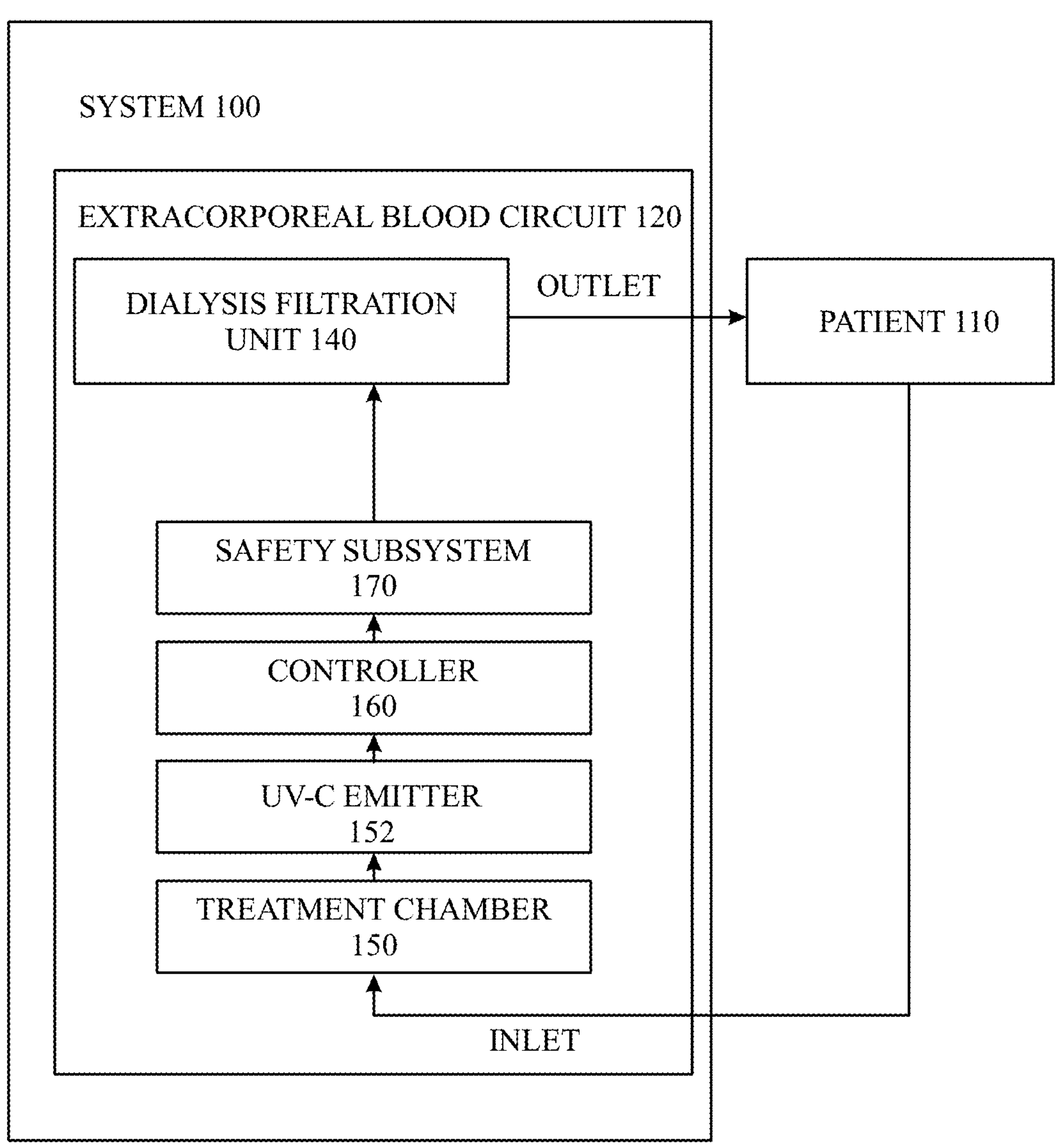
FIG. 1 illustrates a schematic diagram of a system configured for UV-C irradiation of extracorporeal blood in a patient undergoing renal replacement therapy.

The specific details of the single embodiment or variety of embodiments described herein are set forth in this application. Any specific details of the embodiments described herein are used for demonstration purposes only, and no unnecessary limitation(s) or inference(s) are to be understood or imputed therefrom.

Before describing exemplary embodiments in detail, it is noted that the embodiments reside primarily in combinations of components related to devices and systems. Accordingly, the device components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

A system for UV-C blood irradiation may be implemented within a variety of extracorporeal therapy procedures, including but not limited to hemodialysis, hemofiltration, hemodiafiltration, and plasmapheresis. These modalities involve the continuous removal and return of a patient's blood through an external circuit comprising medical-grade tubing, filtration devices, and pumps. The described system incorporates UV-C irradiation into this workflow by enclosing a segment of the blood circuit within a chamber configured to expose circulating blood to germicidal UV-C wavelengths during treatment.

The extracorporeal circuit may include an arterial line to draw blood from the patient, a venous line to return blood, and intermediate components such as a dialyzer or plasma filter. A blood pump may regulate flow rates in the range of approximately 350 mL/min to 400 mL/min. These flow conditions align with standard practice for renal replacement therapy in intensive care or dialysis units.

A treatment chamber may be inserted inline within the blood circuit. This chamber may define a hollow, UV-C transmissive flow path, potentially fabricated from quartz or treated polydimethylsiloxane (PDMS) tubing. The interior of the chamber may be designed to maintain laminar flow and a uniform blood layer thickness, which supports consistent irradiance and mitigates shadowing effects caused by hemoglobin absorption. Baffles or flow guides may be included to minimize turbulence and facilitate uniform exposure.

The chamber may be coupled to one or more UV-C emitters positioned externally and oriented toward the chamber's blood path. The emitters may be mercury quartz burners or UV-C LEDs operating in the 250-270 nm range, with a peak emission wavelength near 262 nm. This germicidal wavelength range targets microbial nucleic acids, forming cyclobutane pyrimidine dimers and 6-4 photoproducts in DNA and RNA, thereby inactivating a broad spectrum of bacteria, viruses, and fungi. The emitters may be housed in a mirrored cylindrical enclosure to enhance irradiance uniformity and reduce energy loss.

An integrated timing mechanism may activate the UV-C emitters for controlled durations based on real-time blood flow metrics. For example, in a 60 kg patient, the system may be configured to irradiate the estimated total body volume, equivalent to 36 L L (alternatively, just plasma volume only~10 L, during a single treatment cycle. The exposure time of this volume can be calibrated to achieve a UV-C dose of 1-20 mJ/cm$^2$, consistent with published thresholds for pathogen inactivation and immune modulation. The dose may be calculated using the formula: Dose (mJ/cm$^2$)=Irradiance (mW/cm$^2$)×Time (seconds). Irradiance levels may be set between 0.25 and 1.0 mW/cm$^2$, depending on desired therapeutic effects.

In some embodiments, the system may include a UV-C module configured to deliver a therapeutic dose ranging from approximately 1-20 mJ/cm$^2$ (10 to 20 mJ/cm$^2$ for pathogen inactivation, or 1 to 5 mJ/cm$^2$ for immune modulation). The treatment chamber may utilize dialysis-compatible tubing segments approximately 20-30 cm in length with an inner diameter of 2 mm, corresponding to a blood volume of approximately 0.628 to 0.942 mL per pass. At a blood flow rate of 250-400 mL/min, blood may reside in the chamber for approximately 0.14 to 0.23 seconds per pass, depending on total volume and flow velocity. When operated at an irradiance of 0.5 mW/cm$^2$, the UV-C dose delivered in a single pass is approximately 0.0705 to 0.113 mJ/cm$^2$. Achieving the therapeutic target may involve increasing irradiance to 2.5 mW/cm$^2$, enhancing internal reflectivity, or cycling blood through multiple passes.

The UV-C chamber may be fabricated from quartz, fluorinated ethylene propylene (FEP), or thermally treated PDMS. These materials exhibit partial to high transparency in the UV-C range and support safe optical coupling between the emitter and the flowing blood. Reflective interiors or mirrored housings may further enhance the efficiency of UV-C delivery to the targeted volume. The geometry of the chamber may promote laminar flow to optimize dose uniformity and minimize scattering and shadowing effects caused by cellular and hemoglobin absorption.

Thermal regulation may be implemented using passive or active cooling mechanisms. The temperature rise per pass through the UV-C chamber is modeled at approximately 0.11° C. With typical therapy durations and continuous flow, total heat rise may remain below 5° C. Inline temperature sensors may monitor outlet temperature, and the system may be configured to automatically halt UV-C emission if blood temperature approaches 40° C., ensuring safe reinfusion into the patient.

Biosensing capabilities may be included to support real-time monitoring and closed-loop control. The system may incorporate sensors to track surrogate biomarkers such as neutrophil reactive oxygen species (ROS), pro-inflammatory cytokines (e.g., IL-6, TNF-α), and lactate levels. A microprocessor-based controller may dynamically adjust UV-C exposure duration or intensity in response to biosensor feedback, thus personalizing the therapy based on the patient's evolving inflammatory and immune profile.

A controller may include a microprocessor configured to receive sensor inputs and regulate the emitter's operation to maintain appropriate exposure. Flow sensors upstream of the treatment chamber may monitor blood velocity and adjust emitter timing accordingly. The controller may also account for patient-specific variables such as hematocrit, total blood volume, and treatment duration.

To maintain clinical safety, a shielding structure may enclose the UV-C source. The shielding may include reflective inner surfaces to concentrate radiation within the chamber while preventing leakage into surrounding environments. The safety subsystem may further include UV sensors to detect stray radiation, thermal sensors to monitor heat generation, and automatic shutdown features in response to system faults or deviations from programmed parameters.

The system may include an optional integrated dosimeter capable of measuring the cumulative UV-C dose delivered during a session. This data may be stored locally or transmitted to external monitoring systems for documentation or dose-response studies. The chamber may be modular and configured for single-use to prevent cross-contamination, or alternatively, it may support sterilization protocols for limited reuse.

In addition to direct pathogen inactivation, the UV-C treatment may also exert immunomodulatory effects. Literature suggests UV-C exposure enhances the phagocytic capacity of neutrophils and dendritic cells, increases intracellular reactive oxygen species (ROS) generation, modulates cytokine profiles, and alters nitric oxide production. Sub-apoptotic UV-C doses ($\leq$0.1 J/cm$^2$) may stimulate pattern recognition receptors (PRRs) while preserving overall immune function.

To reduce clotting risks, citrate anticoagulant may be administered upstream of the treatment chamber, consistent with extracorporeal therapy standards. Blood samples for analysis may be withdrawn from existing catheter access ports, simplifying monitoring and minimizing additional patient discomfort.

The treatment chamber (150) is constructed from UV-transparent quartz or fluoropolymer materials and maintains a narrow, laminar flow path optimized for uniform irradiation. The UV-C emitter (152) is positioned adjacent to the chamber and emits radiation primarily at 262 nm. Internal reflective surfaces enhance dose efficiency while external shielding prevents operator exposure.

The controller (160) interfaces with flow sensors and immune-monitoring modules. In one embodiment, real-time measurement of neutrophil reactive oxygen species (ROS) production or phagocytic capacity downstream of the chamber is used to dynamically regulate exposure time and irradiance. When ROS concentrations or functional indices reach a predefined therapeutic threshold, the controller modulates or halts UV-C exposure.

In another embodiment, the system stratifies patients by sepsis phase using blood biomarkers such as interleukin-6 (IL-6), tumor necrosis factor-alpha (TNF-α), and lactate levels. Based on sepsis severity, the system selects a UV-C dose range: (a) 2-4 mJ/cm$^2$ for early-phase immune activation; (b) 5-10 mJ/cm$^2$ for mid-phase pathogen reduction and cytokine tuning; (c) 0.5-1 mJ/cm$^2$ for late-phase immune suppression reversal. This adaptive dosing enables phase-specific intervention without user recalibration.

In a further embodiment, UV-C irradiation precedes hemofiltration within the circuit. This order ensures that pathogen components or immune-reactive byproducts resulting from UV exposure are subsequently removed by the filtration membrane, enhancing detoxification and reducing inflammatory sequelae.

Additionally, the system may include inputs for patient-specific hematocrit levels and polymorphisms in DNA repair genes such as XRCC1 or ERCC2. These inputs inform personalized modulation of UV-C dose, mitigating risk to sensitive immune cells while preserving treatment efficacy.

The device supports closed-loop control and may log treatment data including UV-C dose, flow rate, and biomarker changes. In one variation, an integrated dosimeter provides cumulative energy delivery information. Single-use treatment chambers may be implemented to ensure sterility and prevent cross-contamination.

Through integration of immunological feedback, biomarker stratification, and sequencing logic, the disclosed UV-C system enables novel immunotherapeutic interventions in extracorporeal sepsis management while maintaining compatibility with existing renal therapy workflows.

The system may be adapted for use in plasma-based treatments by replacing the blood chamber with a UV-C-compatible plasma flow path. This configuration may enable pathogen reduction in plasma exchange or plasmapheresis applications.

In some embodiments, UV-C parameters, including irradiance, exposure time, and target dose, may be adjusted depending on treatment goals. Lower doses (e.g., 1-5 mJ/cm$^2$) may support immune modulation, while higher doses (e.g., 10-20 mJ/cm$^2$) may target pathogen clearance in acute sepsis.

In some embodiments, the disclosed system includes a UV-C treatment chamber fabricated from materials that exhibit high transmissivity to ultraviolet C wavelengths in the 250-270 nm range. Suitable materials include quartz, fluoropolymers such as fluorinated ethylene propylene (FEP), or polydimethylsiloxane (PDMS). These materials ensure minimal UV attenuation and allow consistent exposure across the blood flow path. The chamber geometry may be cylindrical or rectangular, and optimized to maintain laminar flow and reduce turbulence, thus promoting uniform irradiation and preventing shadowing of blood components.

To facilitate immune modulation, a solid-state UV-C LED emitter or mercury quartz burner may be arranged adjacent to or around the treatment chamber. The LED array may be configured to emit at a peak wavelength of approximately 262 nanometers, which aligns with the known germicidal peak effective against bacterial DNA and viral RNA. In one embodiment, the UV-C emitter delivers a dose of approximately 5 to 10 mJ/cm$^2$ over a 10-second exposure period as blood flows through the chamber at 250-400 mL/min, enabled by a blood pump or flow regulator in the extracorporeal circuit.

Real-time biosensors are positioned downstream of the treatment chamber to monitor neutrophil reactive oxygen species (ROS) levels or phagocytic activity. These sensors may employ chemiluminescent probes or electrochemical detection platforms to quantify ROS as a signal of immune cell activation. The system uses these signals to dynamically adjust or terminate UV-C exposure via a microprocessor-based controller. When a threshold ROS concentration is reached, the controller halts emitter operation, ensuring therapeutic effect while avoiding immune overstimulation. The controller is also configured to store session data in local or remote memory for clinical analysis.

In another configuration, the system is used to enhance endotoxin clearance during extracorporeal therapy such as hemofiltration. In these embodiments, UV-C irradiation precedes blood filtration, and is specifically performed before the blood reaches the hemofilter. The emitter irradiates blood for a duration between 6 and 12 seconds, which has been found sufficient to fragment lipopolysaccharides (LPS) and other endotoxins while preserving red blood cell integrity.

The hemofilter used in this process may comprise a membrane with a molecular weight cutoff between 70 and 100 kilodaltons, allowing for the selective removal of damaged microbial components, pro-inflammatory cytokines, and endotoxin fragments generated during UV-C exposure. In some embodiments, the hemofilter is constructed from polysulfone or polyether sulfone, materials that are both biocompatible and durable under clinical flow conditions.

The UV-C emitter may be enclosed in a reflective housing to amplify dose uniformity. Polished aluminum or mirrored stainless steel surfaces may be used to reflect UV-C radiation back through the treatment chamber, improving irradiance without increasing power input. A temperature sensor integrated into the emitter housing, or the chamber wall provides feedback to the safety subsystem, which automatically shuts off the emitter if the operating temperature exceeds a defined limit, such as 42° C., to prevent thermal damage to blood proteins or cells.

A flow sensor upstream of the chamber detects the presence of moving blood. When flow begins, the sensor transmits a signal to the controller, which in turn triggers UV-C emission automatically, thus reducing reliance on manual activation and ensuring consistency in treatment delivery. In some configurations, the system includes an integrated dosimeter to measure the cumulative UV-C dose delivered per session, along with the total volume of blood treated. These metrics may be logged in a session-based record stored in the controller's internal memory or transmitted wirelessly to an electronic medical record (EMR) system or clinical dashboard.

In some embodiments, a user interface allows clinicians to review real-time treatment data, modify exposure parameters, or enable/disable automatic safety functions. The user interface may display current ROS levels, emitter status, cumulative dose, and blood flow metrics to provide full visibility into treatment progression and patient response.

By integrating both immune feedback regulation and sequential UV-C and hemofilter exposure, the disclosed system supports precision interventions in septic patients. These dependent claim features enable controlled blood irradiation tailored to both immunomodulation goals and endotoxin clearance, expanding the system's applicability across different phases of sepsis and extracorporeal therapy protocols.

In an additional embodiment, the disclosed system may be used to treat carbon monoxide (CO) poisoning through extracorporeal exposure of blood to selected visible wavelengths. Carbon monoxide binds to hemoglobin with over 200 times the affinity of oxygen, forming carboxyhemoglobin (CO-Hb) and preventing oxygen delivery to tissues. It also binds to the heme iron of cytochrome oxidase (Complex IV) in mitochondria, halting electron transport and cellular respiration.

To overcome the limited tissue penetration of light in traditional therapies, this system irradiates extracorporeal blood directly, using calibrated light delivery. The device includes LEDs or laser sources emitting at two key therapeutic bands: 540-580 nm to target carboxyhemoglobin dissociation, and 420-450 nm (Soret band) to reverse CO inhibition of cytochrome oxidase. Light is delivered through UV-visible transparent tubing made from fluorinated ethylene propylene (FEP) or similar, ideally $\leq$3 mm in diameter to permit light penetration.

The tubing may be wrapped around a broadband emitter or placed within a cylindrical light bath with reflective shielding. Exposure is controlled to deliver 100-250 mW/cm$^2$ irradiance and 5-15 J/cm$^2$ dose per pass, with real-time calculation based on blood flow rate and tubing geometry. In some embodiments, inline co-oximetry modules measure CO-Hb saturation continuously using differential spectrophotometry. These data are fed into the system controller to dynamically adjust the duration, sequence, and intensity of 540-580 nm and 420-450 nm irradiation. Optional mitochondrial function sensors using cytochrome redox state monitoring can be included for enhanced feedback on cytochrome oxidase recovery.

In certain configurations, the system may be extended with an optional photodissociation module for treating carbon monoxide (CO) poisoning. This module may employ dual-wavelength light sources emitting in the 420-450 nm range (targeting cytochrome oxidase) and the 540-580 nm range (targeting carboxyhemoglobin). These emitters may be configured to deliver 0.47-1.2 J/mL per pass at power densities between 100-250 mW/cm$^2$. Therapeutic goals for CO elimination typically require a cumulative dose exceeding 20 J/mL, which may be achieved over approximately 20-40 passes through the irradiation chamber during 90-120 minutes of continuous circulation.

The photodissociation module may include a fiberoptic light delivery sheath or reflective cylindrical housing surrounding the flow path. This chamber may be placed upstream or downstream of a membrane oxygenator that delivers 100% oxygen at 2-5 L/min. The oxygenation subsystem may be selected to maintain blood partial pressure of oxygen ($pO_2$) above 500 mmHg, promoting the dissociation of carbon monoxide from hemoglobin and mitochondrial enzymes by mass action. A co-oximetry system may be included to monitor the fractional concentration of CO-bound hemoglobin in real time and support dynamic therapy adjustment.

The entire circuit may be designed for compatibility with standard dialysis catheters, such as dual-lumen 14.5 French access lines, and may support heparin or citrate-based anticoagulation regimens. The system may include air detectors, automatic shut-off valves, and logging interfaces to track treatment metrics such as total dose, therapy duration, and biosensor trends. Setup and teardown of the extracorporeal circuit may be completed within approximately 60 minutes using sterile field protocols, allowing rapid deployment in critical care settings.

Clinical Use Scenarios

The disclosed extracorporeal blood treatment system may be deployed across various clinical settings, including emergency departments, intensive care units, and inpatient dialysis facilities. The modular design allows integration with both renal replacement therapy (RRT) platforms and standalone extracorporeal circuits. Below are exemplary clinical scenarios illustrating how the system may be configured and used.

Case Example 1—Sepsis During Renal Replacement Therapy

In an emergency department of a regional hospital, a 50-year-old male patient with known end-stage renal disease presents with fever, hypotension, and tachycardia during a scheduled hemodialysis session. Blood cultures are obtained, and he is diagnosed with septicemia. Intravenous antibiotics are initiated promptly. Because the patient already has an arteriovenous fistula in place, dialysis is resumed using the existing extracorporeal access. The disclosed system is attached in-line to the dialysis circuit and activated in sepsis mode. UV-C light is delivered at a wavelength of approximately 262 nm, with a target dose of 5-10 mJ/$cm^2$ per protocol. The treatment chamber, composed of UV-transmissive material and integrated with reflective shielding, allows pathogen inactivation and immunomodulation to occur concurrently with ongoing hemodialysis. Real-time biosensor data, such as reactive oxygen species (ROS) and inflammatory cytokine levels, may guide dynamic dose adjustments via the system controller.

Case Example 2—Sepsis Without Renal Indication

In the intensive care unit of the same hospital, a 20-year-old female patient is intubated for pneumonia and has developed persistent sepsis despite antibiotic therapy. She does not require dialysis and has no prior renal disease. To enable extracorporeal therapy, a temporary dual-lumen catheter is inserted into a central vein (e.g., jugular or femoral). The disclosed system is deployed independently of any dialysis platform. In sepsis mode, UV-C therapy is initiated with a blood flow rate maintained at 250 mL/min. The UV-C emitter operates in a pulsed or continuous mode to deliver sub-cytotoxic doses across multiple passes, enhancing neutrophil activation and reducing microbial burden. Thermal sensors ensure outlet blood temperature remains below 40° C., and inline monitoring enables personalized treatment duration. The system operates as a standalone adjunct to standard antimicrobial therapy.

Case Example 3—Carbon Monoxide (CO) Poisoning

A 60-year-old male is brought in by ambulance after being found unconscious in his residence, where emergency responders identify a malfunctioning gas heater. Carboxyhemoglobin (CO-Hb) levels are elevated, confirming carbon monoxide poisoning. Although high-flow oxygen therapy is started, the care team initiates extracorporeal therapy by inserting a temporary central venous catheter. The disclosed system is configured in CO poisoning mode. A dual-wavelength photodissociation module is activated, emitting light in the 420-450 nm and 540-580 nm ranges. This light selectively dissociates CO from hemoglobin and cytochrome oxidase. A hollow-fiber membrane oxygenator connected upstream of the light chamber maintains blood $pO_2$ above 500 mmHg to enhance CO elimination via mass action. A co-oximetry sensor monitors CO-Hb levels in real-time, and the controller dynamically modulates light exposure based on feedback. Treatment continues until therapeutic thresholds are achieved, typically over 90-120 minutes of circulation.

FIG. 1 a schematic diagram of a system 100 configured for ultraviolet C (UV-C) irradiation of extracorporeal blood in a patient undergoing renal replacement therapy. The system includes a patient 110 connected to an extracorporeal blood circuit 120, which facilitates the continuous withdrawal and return of blood during treatment. The extracorporeal circuit 120 may be constructed of sterile medical-grade tubing compatible with high-volume blood flow and is fluidly coupled to a dialysis filtration unit 140. The filtration unit 140 may include a dialyzer or hemofilter configured to remove toxins, solutes, or excess fluids from the patient's blood as part of hemodialysis, hemofiltration, or hemodiafiltration procedures. Integrated within the extracorporeal blood circuit 120 is a treatment chamber 150. This chamber is configured to receive a portion of the circulating blood and expose it to germicidal UV-C radiation. The treatment chamber 150 may include a UV-C emitter 152 positioned adjacent to or surrounding a portion of the blood flow path. The emitter 152 is configured to emit radiation within the range of 250 nanometers (nm) to 270 nm, which corresponds to the germicidal UV-C spectrum, with a peak efficacy wavelength around 262 nm. The emitter may be a mercury quartz burner or solid-state UV-C LED and may be enclosed in a reflective housing to optimize irradiation uniformity and prevent environmental leakage. The emitter 152 is operably controlled by a controller 160, which may include a microprocessor or programmable logic controller configured to regulate emitter operation based on system inputs such as flow rate and treatment duration. The controller 160 ensures that blood is exposed to UV-C for an appropriate duration, typically about 10 seconds per treated blood unit, and may coordinate with flow sensors to synchronize activation with real-time blood velocity. A safety subsystem 170 is operably coupled to both the emitter 152 and controller 160. The safety subsystem may include sensors to detect UV-C leakage, monitor temperature near the treatment site, and verify emitter status. Upon detecting abnormal conditions, the safety subsystem 170 may automatically deactivate the emitter 152 to prevent harm to the patient or clinical personnel. The system may be configured to treat only a defined portion of the patient's blood volume per cycle, such as 3.5 mL per kilogram of body weight, to minimize potential cytotoxicity while achieving desired immunomodulatory and antimicrobial effects. Following UV-C exposure in the treatment chamber 150, the irradiated blood is routed through the outlet line of the extracorporeal blood circuit 120 and returned to the patient 110, completing the circulation loop.

Figure 2:
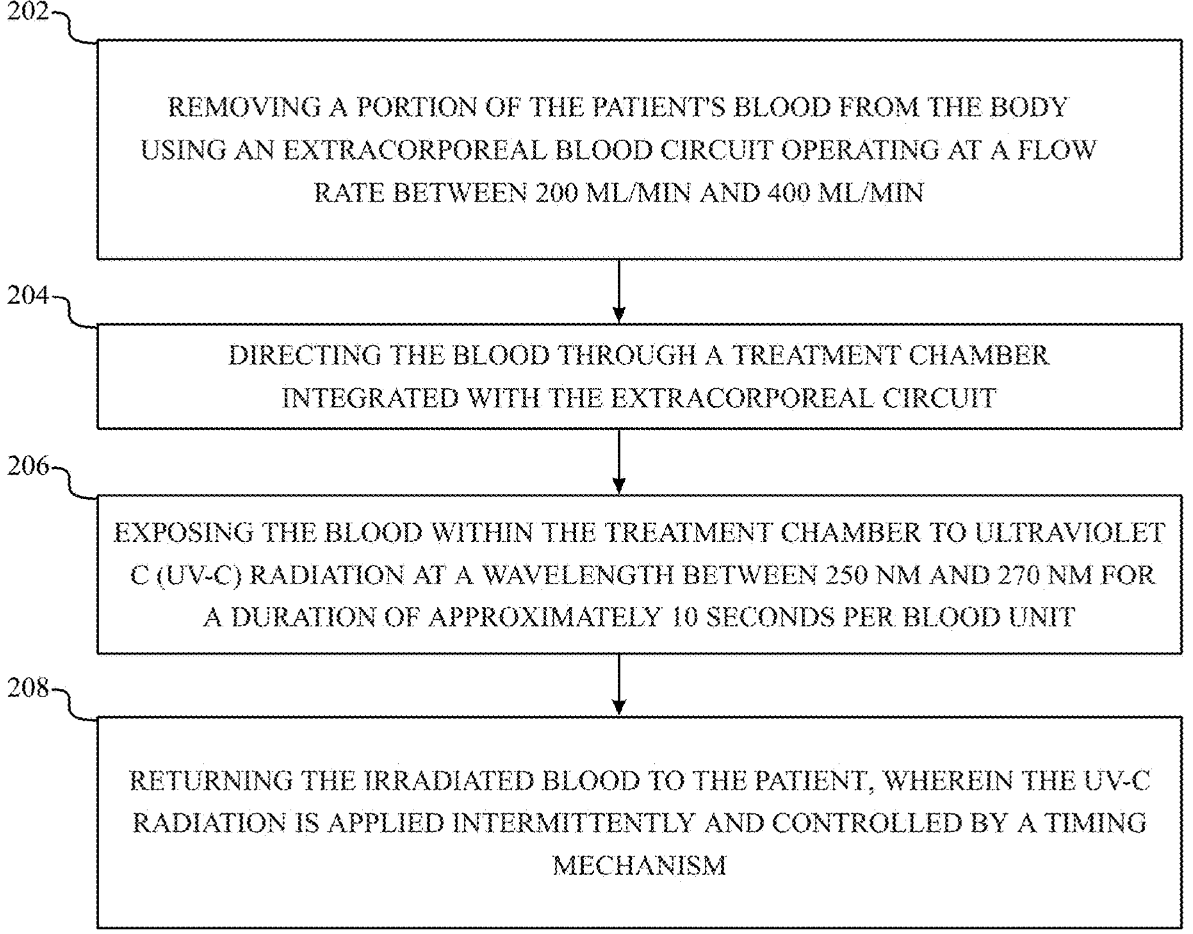
FIG. 2 illustrates a process diagram of a method for reducing pathogen load in a patient undergoing extracorporeal blood treatment, in accordance with an embodiment of the disclosed system.

FIG. 2 illustrates a process diagram of a method for reducing pathogen load in a patient undergoing extracorporeal blood treatment, in accordance with an embodiment of the disclosed system. The illustrated method corresponds to a sequence of steps that may be performed using a UV-C irradiation subsystem integrated into a renal replacement therapy circuit.

At step 202, a portion of the patient's blood is removed from the body using an extracorporeal blood circuit. The circuit may include a sterile arterial access line, blood pump, and medical-grade tubing, and is configured to maintain a blood flow rate between approximately 200-400 ml/min. This range reflects common clinical parameters used during continuous renal replacement therapy (CRRT) or intermittent hemodialysis.

At step 204, the removed blood is directed through a treatment chamber integrated with the extracorporeal circuit. The treatment chamber may include a UV-C transmissive flow path constructed of materials such as quartz or polydimethylsiloxane (PDMS) and is shaped to maintain a controlled laminar flow of blood for consistent radiation exposure. The geometry and flow mechanics within the chamber ensure even irradiance across the blood volume.

At step 206, the blood is exposed to ultraviolet C (UV-C) radiation within the treatment chamber. The UV-C radiation may be emitted by one or more emitters positioned around or adjacent to the chamber. These emitters are configured to operate at wavelengths between 250 nanometers and 270 nanometers, with a peak germicidal wavelength around 262 nanometers. The emitters may be mercury vapor lamps or solid-state UV-C LEDs capable of delivering a sufficient dose to inactivate viruses, bacteria, or fungi present in the bloodstream. The exposure duration for each unit of blood is approximately 10 seconds, allowing sufficient time for DNA and RNA damage to occur in microbial cells while minimizing impact on anucleate red blood cells and immune components.

The radiation is applied intermittently and governed by a timing mechanism that may receive real-time input from flow sensors or a system controller. The controller may calculate exposure parameters to ensure the UV-C treatment is limited to a predefined blood volume. In particular, the method restricts treatment to approximately 3.5 milliliters of blood per kilogram of the patient's body weight during a single cycle. This threshold is based on prior clinical research identifying optimal therapeutic windows for ultraviolet blood irradiation without compromising cellular viability or function.

At step 208, the irradiated blood is returned to the patient through the venous return line of the extracorporeal circuit. The system may continuously cycle blood through the treatment process until the targeted volume has been irradiated. Safety measures, including UV shielding and emitter shutoff controls, may be integrated to prevent overexposure or leakage of radiation into surrounding environments.

Figure 3:
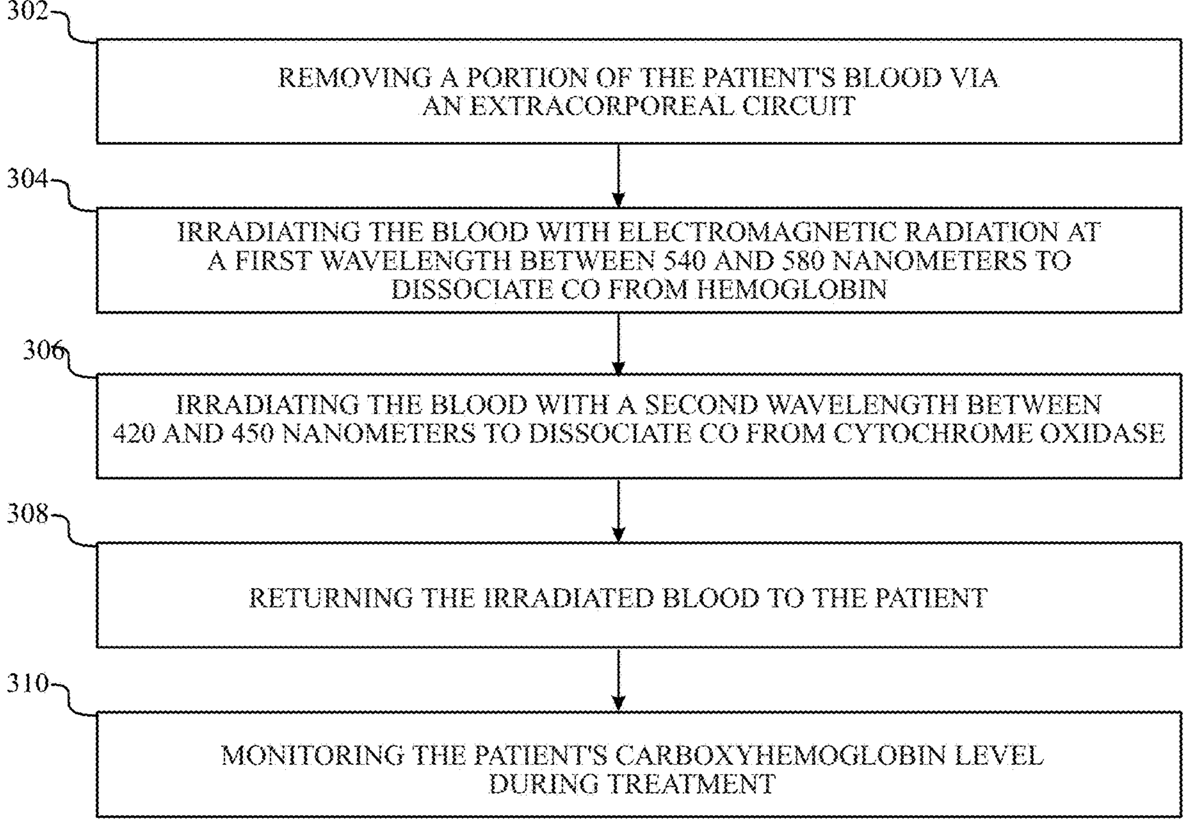
FIG. 3 illustrates a process diagram of a method for treating carbon monoxide (CO) poisoning using extracorporeal irradiation of blood, in accordance with an embodiment of the disclosed system, in accordance with an embodiment of the disclosed system.

FIG. 3 illustrates a process diagram of a method for treating carbon monoxide (CO) poisoning using extracorporeal irradiation of blood, in accordance with an embodiment of the disclosed system. The illustrated method sequence includes key steps necessary to dissociate CO from its high-affinity binding sites on hemoglobin and cytochrome oxidase enzymes through controlled exposure to therapeutic wavelengths of light.

At step 302, a portion of the patient's blood is removed from the body using an extracorporeal blood circuit. This circuit may include arterial access tubing, medical-grade connectors, and a blood pump to maintain continuous flow. The system is configured to preserve hemodynamic stability while directing blood toward an illumination chamber optimized for optical exposure.

At step 304, the removed blood is irradiated with electromagnetic radiation at a first wavelength between approximately 540 and 580 nanometers. This spectral range corresponds to the differential absorption of carboxyhemoglobin (CO-Hb) versus oxyhemoglobin and is selected to efficiently dissociate CO from the iron center of the hemoglobin molecule. Light may be delivered via LED arrays or laser sources situated around a transparent section of the blood flow path.

At step 306, the blood is further irradiated with a second wavelength between approximately 420 and 450 nanometers, which corresponds to the Soret band of cytochrome oxidase. This exposure breaks the CO-heme bond at the cytochrome $a_3$ subunit of complex IV, restoring electron transport and enabling cellular respiration to resume. Both wavelengths may be applied simultaneously or sequentially, depending on emitter design and system calibration.

At step 308, the irradiated blood is returned to the patient through the venous return line of the extracorporeal circuit. This step ensures that reoxygenated and detoxified blood is promptly reintroduced into the circulatory system to mitigate the hypoxic effects of CO poisoning.

At step 310, the system monitors the patient's carboxyhemoglobin levels during treatment. This may be achieved through integrated co-oximetry sensors, which allow real-time analysis of CO-Hb dissociation. Based on the monitored values, the controller may adjust light dosage, exposure duration, or treatment repetition in a closed-loop manner.

The illustrated process provides a non-invasive, extracorporeal means of accelerating CO clearance from the bloodstream, supplementing or replacing traditional oxygen-based therapies. By utilizing targeted photodissociation, the system enables rapid and effective treatment of CO poisoning with precision dosing and real-time biochemical monitoring.

In this disclosure, the descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Thus, the appended claims should be construed broadly, to include other variants and embodiments, which may be made by those skilled in the art.

It will be appreciated by persons skilled in the art that the present embodiment is not limited to what has been particularly shown and described hereinabove. A variety of modifications and variations are possible considering the above teachings without departing from the following claims.

I claim:

1. A method of modulating immune cell activity in a septic patient undergoing extracorporeal therapy, the method comprising:

removing a portion of the patient's blood using an extracorporeal circuit;

exposing the blood to UV-C radiation in the 250-270 nm range;

adjusting exposure duration and intensity based on real-time detection of neutrophil ROS levels or phagocytic activity; and returning the irradiated blood to the patient; and wherein the real-time detection of neutrophil reactive oxygen species (ROS) levels is performed by an in-line biosensor downstream of the UV-C exposure site.

2. The method of claim 1, wherein the UV-C radiation is delivered at approximately 262 nm.

3. The method of claim 1, wherein exposure duration is terminated upon reaching a threshold ROS concentration.

4. The method of claim 1, wherein the extracorporeal circuit comprises a treatment chamber fabricated from a UV-transmissive material selected from the group consisting of quartz, fluoropolymer, and polydimethylsiloxane (PDMS).

5. The method of claim 1, wherein the UV-C radiation is delivered by a solid-state UV-C light-emitting diode (LED) array configured to emit at a peak wavelength of approximately 262 nanometers.

6. The method of claim 1, further comprising regulating the UV-C exposure duration using a microprocessor-based controller programmed to halt irradiation when ROS levels exceed a therapeutic threshold.

7. The method of claim 1, wherein the total blood volume treated during a single therapy session is limited to approximately 3.5 milliliters per kilogram of the patient's body weight.

8. The method of claim 1, wherein the blood is irradiated for a duration of approximately 10 seconds while flowing at a rate between 350 and 400 milliliters per minute.

* * * * *